United States Patent
Till et al.

(10) Patent No.: US 8,405,826 B2
(45) Date of Patent: Mar. 26, 2013

(54) METHOD FOR THE INSPECTION OF BOTTLES OR CONTAINERS IN A BOTTLING OR CONTAINER FILLING PLANT AND AN APPARATUS FOR THE INSPECTION OF BOTTLES OR CONTAINERS

(75) Inventors: Volker Till, Hofheim am Taunus (DE); Paul-Gerhard Kahlisch, Fröndenberg (DE); Horst Böcker, Schwerte (DE)

(73) Assignee: KHS GmbH, Dortmund (DE)

( * ) Notice: Subject to any disclaimer, the term of this patent is extended or adjusted under 35 U.S.C. 154(b) by 432 days.

(21) Appl. No.: 12/466,485

(22) Filed: May 15, 2009

(65) Prior Publication Data
US 2009/0279082 A1    Nov. 12, 2009

(30) Foreign Application Priority Data
Nov. 15, 2006   (DE) .................. 10 2006 054 099

(51) Int. Cl.
*G01N 21/00* (2006.01)
(52) U.S. Cl. ............... 356/240.1; 356/237.1; 356/237.6
(58) Field of Classification Search .... 356/237.1–237.6, 356/240.1
See application file for complete search history.

(56) References Cited

U.S. PATENT DOCUMENTS

| | | | |
|---|---|---|---|
| 3,557,950 | A | 1/1971 | Powers |
| 4,136,930 | A | 1/1979 | Gomm et al. |
| 4,209,802 | A | 6/1980 | Brandt et al. |
| 4,605,851 | A | 8/1986 | Ometz et al. |
| 4,801,319 | A | 1/1989 | Rugaber et al. |
| 4,902,137 | A | 2/1990 | Krieg et al. |
| 5,492,216 | A | 2/1996 | McCoy et al. |
| 5,495,330 | A * | 2/1996 | Champaneri et al. ...... 356/240.1 |
| 5,917,602 | A | 6/1999 | Bonewitz et al. |
| 5,926,268 | A | 7/1999 | Bonewitz et al. |

(Continued)

FOREIGN PATENT DOCUMENTS

| | | |
|---|---|---|
| DE | 299 19 761 | 12/2000 |
| DE | 10 2004 051 961 | 5/2006 |

(Continued)

OTHER PUBLICATIONS

Chinese Office Action 200780042554.6 and English translation thereof.

(Continued)

*Primary Examiner* — Tarifur Chowdhury
*Assistant Examiner* — Isiaka Akanbi
(74) *Attorney, Agent, or Firm* — Nils H. Ljungman & Associates

(57) ABSTRACT

A method for the inspection of bottles or containers in a bottling or container filling plant and an apparatus for the inspection of bottles or containers. The abstract of the disclosure is submitted herewith as required by 37 C.F.R. §1.72(b). As stated in 37 C.F.R. §1.72(b): A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims. Therefore, any statements made relating to the abstract are not intended to limit the claims in any manner and should not be interpreted as limiting the claims in any manner.

23 Claims, 4 Drawing Sheets

U.S. PATENT DOCUMENTS

| | | | |
|---|---|---|---|
| 6,025,910 A * | 2/2000 | Lucas | 356/240.1 |
| 6,049,585 A * | 4/2000 | Ocleppo | 378/57 |
| 6,260,425 B1 | 7/2001 | Eder | |
| 6,914,672 B2 * | 7/2005 | Yagita | 356/239.5 |
| 7,497,237 B2 * | 3/2009 | Till | 141/5 |
| 2005/0263443 A1 | 12/2005 | Martin et al. | |
| 2008/0291438 A1 * | 11/2008 | Akkerman et al. | 356/240.1 |

FOREIGN PATENT DOCUMENTS

| | | |
|---|---|---|
| EP | 0 124 164 | 11/1984 |
| EP | 0 277 629 | 8/1988 |
| EP | 1 493 690 | 1/2005 |
| EP | 1 700 643 | 9/2006 |
| FR | 2 746 502 | 9/1997 |
| JP | 9236553 | 9/1997 |
| JP | 11337505 | 12/1999 |
| RU | 2142860 C1 | 12/1999 |
| WO | WO 96/18883 | 6/1996 |
| WO | WO 01/44791 | 6/2001 |

OTHER PUBLICATIONS

International Search Report PCT/EP2007/009633 and English translation thereof.

International Preliminary Report on Patentability PCT/EP2007/009633 and English translation thereof.

* cited by examiner

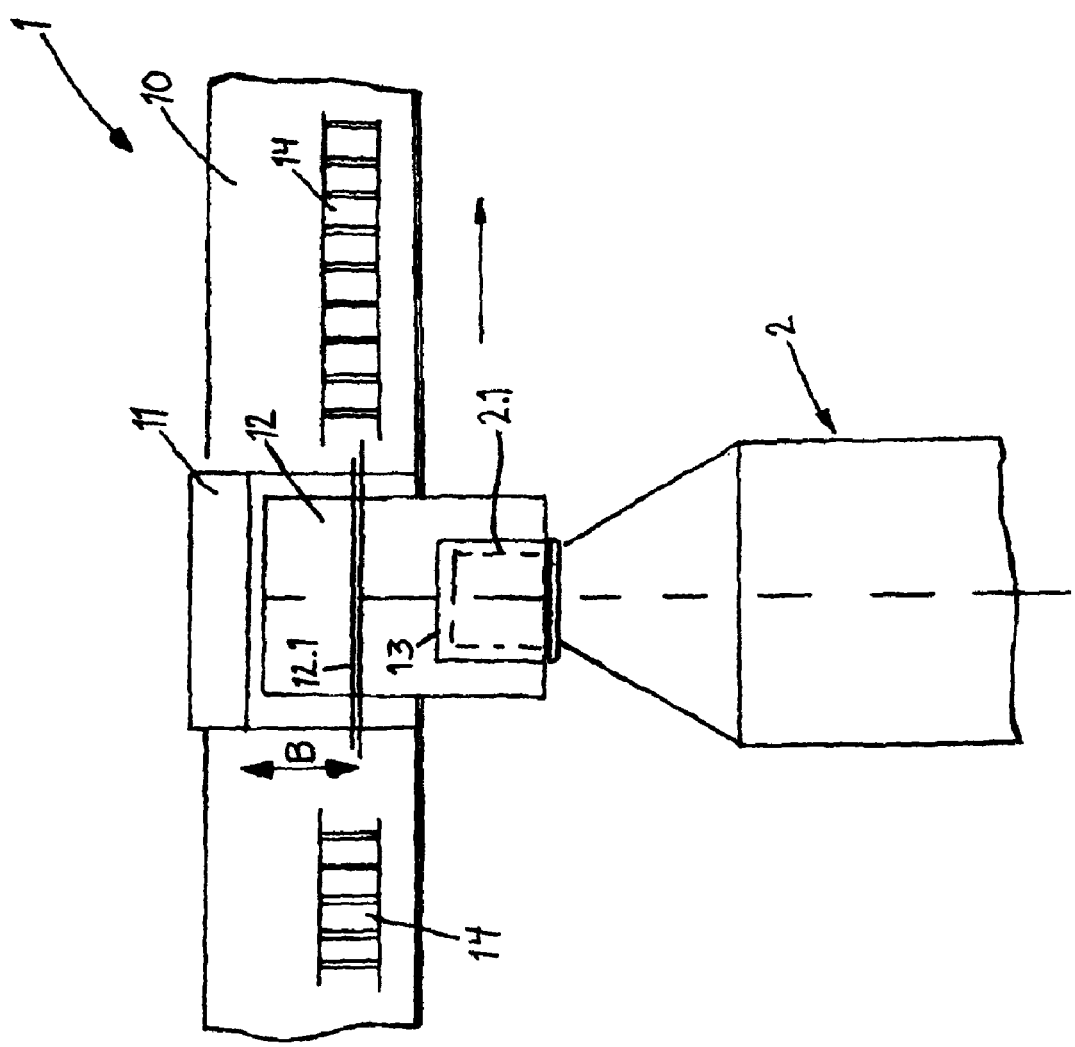

US 8,405,826 B2

METHOD FOR THE INSPECTION OF BOTTLES OR CONTAINERS IN A BOTTLING OR CONTAINER FILLING PLANT AND AN APPARATUS FOR THE INSPECTION OF BOTTLES OR CONTAINERS

CONTINUING APPLICATION DATA

This application is a Continuation-In-Part application of International Patent Application No. PCT/EP2007/009633, filed on Nov. 7, 2007, which claims priority from Federal Republic of Germany Patent Application No. 10 2006 054 099.9, filed on Nov. 15, 2006. International Patent Application No. PCT/EP2007/009633 was pending as of the filing date of this application. The United States was an elected state in International Patent Application No. PCT/EP2007/009633.

BACKGROUND

1. Technical Field

The present application relates to a method for the inspection of bottles or containers in a bottling or container filling plant and an apparatus for the inspection of bottles or containers.

2. Background Information

Background information is for informational purposes only and does not necessarily admit that subsequently mentioned information and publications are prior art.

The present application relates to a method for the inspection of bottles or similar containers filled with a pourable liquid being bottled, whereby the containers are inspected with an opto-electrical or electromagnetic imaging and processing or analysis system to detect any solid or foreign objects that may be housed in the pourable liquid being bottled, and to an apparatus for the inspection of bottles or similar containers, for example to a full-bottle or full-container inspector described as either an apparatus for the inspection of bottles or similar containers filled with a liquid, with an opto-electrical or electromagnetic imaging and processing or analysis system for the detection of any solid matter or foreign objects that may be present in the bottled liquid, or and inspection apparatus for the inspection of containers, whereby the containers are held by a holding device and are moved along a treatment or inspection line by means of a linear movement, whereby the containers are guided along at least one inspection station. An inspection apparatus is the object of an apparatus for the inspection of bottles or similar containers filled with a liquid, with an opto-electrical or electromagnetic imaging and processing or analysis system for the imaging of any solid matter or foreign objects that may be present in the bottled liquid, and with a transport system, with which the containers are moved for the inspection on a transport or inspection line, and with a ramp that forms a container inlet and a container outlet of the transport system, which ramp is connected to an external conveyor for the delivery and removal of the containers.

OBJECT OR OBJECTS

An object of the present application is to describe a method which makes possible a reliable inspection of containers filled with a liquid or a pourable liquid product (including full bottles or full containers) for the presence of any solid or foreign articles that may be present at a high rate of production (number of containers inspected per unit of time). Another object of the present application is the reliable detection of any foreign objects in filled bottles or containers, which means in one possible embodiment that it must be possible to reliably detect even foreign objects that have relatively small diameters.

SUMMARY

To accomplish this object, the present application teaches a method for the inspection of bottles or similar containers filled with a pourable liquid being bottled. The containers are inspected with an opto-electrical or electromagnetic imaging and processing or analysis system to detect any solid or foreign objects that may be housed in the pourable liquid being bottled. A reference image is generated of each container in a first container orientation with an opto-electrical or electromagnetic sensor. Then at least one additional image of each container is generated in at least one additional orientation which differs from the first container orientation with the opto-electrical or electromagnetic sensor. The inspection for potential foreign objects is performed by processing and/or comparison of the reference image with the at least one additional image. An inspection apparatus is the object of an apparatus for the inspection of bottles or similar containers filled with a liquid, with an opto-electrical or electromagnetic imaging and processing or analysis system for the detection of any solid matter or foreign objects that may be present in the bottled liquid. The inspection apparatus comprises an opto-electrical or electromagnetic sensor system with which, in a first container orientation, a reference image of each container is generated. Then in at least one additional container orientation that varies from the first orientation, at least one additional image is generated. The inspection apparatus also comprises an electronic system for the analysis of the images for the monitoring for possible foreign objects. An inspection apparatus is also the object of an inspection apparatus for the inspection of containers. The containers are held by a holding device and are moved along a treatment or inspection line by means of a linear movement. The containers are guided along at least one inspection station. Within the inspection apparatus a flexible element is provided on which the containers are held and by means of which the containers are moved along the treatment line.

In the present application, the inspection of the containers is performed by imaging and image evaluation or analysis, and in at least one possible embodiment by generating a reference image of each container in a reference position or orientation of the container and then comparing this reference image with at least one additional image, which is also called a comparison or inspection image, which was generated of the same container in a position or orientation in three-dimensional space that differs from the reference orientation, whereby the image plane of the area of the container which is reproduced in the processed or compared images (reference image and the at least one additional image of the respective container) or in images derived from it is identical or essentially identical. In the simplest case the different container orientation in the space during the imaging, with the preservation of the same image plane, can be accomplished for example, by pivoting the container in question out of its reference orientation around an axis which is parallel or essentially parallel both to the optical axis of the opto-electrical sensor that generates the reference image as well as parallel or essentially parallel to the optical axis of the opto-electrical sensor that generates the at least one inspection image.

The image areas of the respective container that are recorded by the opto-electrical sensors and/or during the image processing are thereby in at least one possible embodiment identical or practically identical, so that during the evaluation of the reference image and of the at least one inspection image, defects in the respective container itself, such as, for example, bubbles and/or inclusions in the container wall, mold seams, notches, scratches, etc., can be eliminated as image components that are acceptable for purposes of the inspection and need not be taken or may not need to be taken into consideration in the evaluation of the images.

In the method of the present application, at least one additional image is generated in at least one additional container orientation which differs from the first container orientation.

In one possible embodiment of the present application, the container orientation is varied by pivoting and/or the reference image and the at least one additional image are generated chronologically one after the other with different opto-electrical or electromagnetic sensors.

The object of the present application can be reliably accomplished with a reference method in which a reference image and at least one additional image are produced of one and the same area of the container, and these images are compared in an image processing and analysis if the images are taken or generated in different container orientations, i.e. with a different orientation of the container axis of the respective container, e.g. before and after the tipping or pivoting of the respective container.

Because foreign objects in filled containers will with a high degree of probability settle on the bottom of the container, tipping the respective container causes an accumulation of these foreign objects in an area between the bottom of the container and the adjacent container wall, so that as a result of the different container orientation during the recording of the reference image and the subsequent recording of at least one additional image (comparison or inspection image), images are obtained which differ significantly when solid objects or foreign objects are present in the container. Even small quantities of foreign objects in a container are thereby reliably detected.

The transport system of the present application is realized for a pivoting of the containers so that the at least one additional image can be generated in a container orientation which is different from the first container orientation.

The flexible element of the present application is provided with grippers which act as the holding apparatus for the containers 2.

The ramp of the present application can be modified so that the containers are transported past the inspection line on the external conveyor.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

Developments of the present application are described according to the present application. The present application is described in greater detail below with reference to one possible embodiment illustrated in the accompanying figures, in which:

FIG. 2 is a detail of one of the transport elements or a slide of the transport system of the inspection apparatus illustrated in FIG. 1, together with a bottle;

DESCRIPTION OF EMBODIMENT OR EMBODIMENTS

Figure 1:
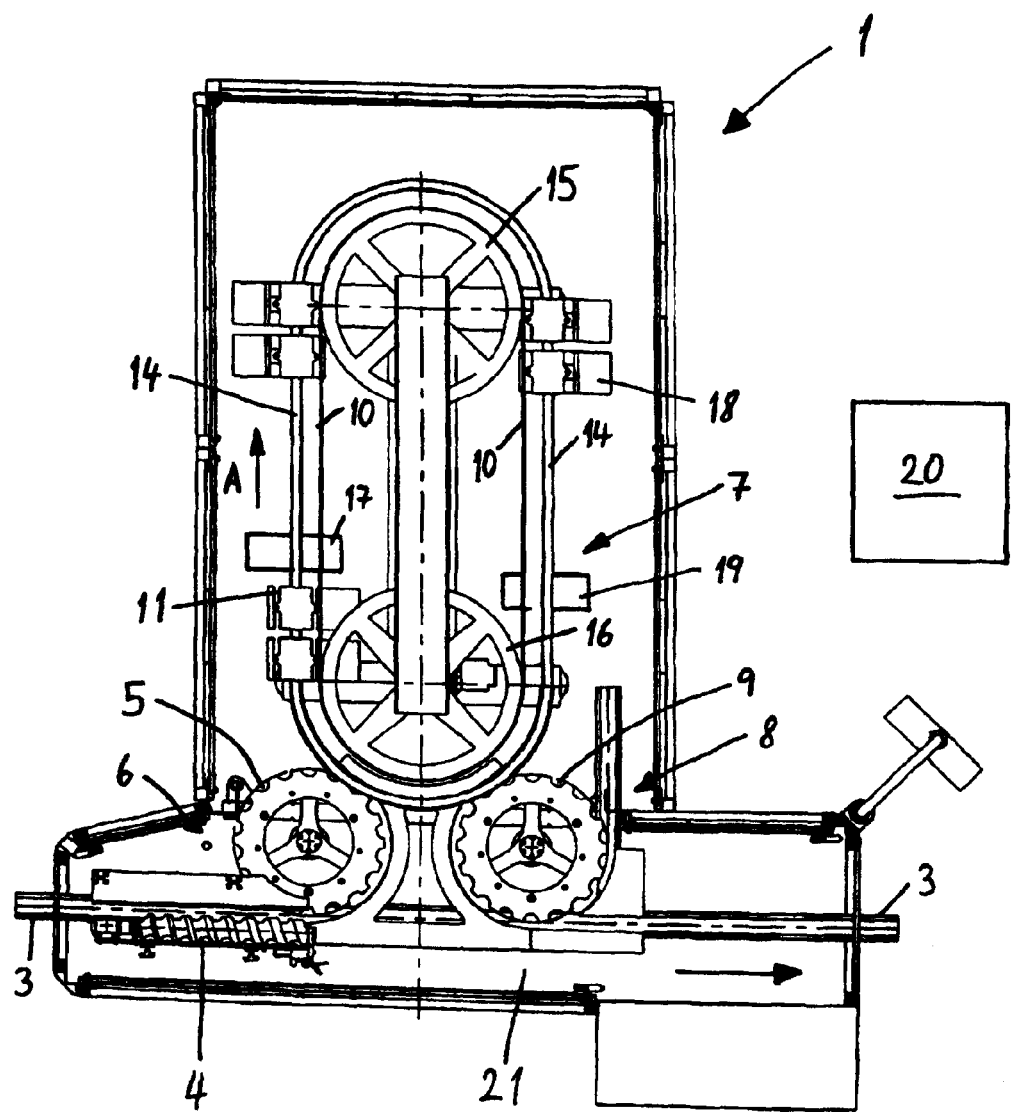
FIG. 1 is a schematic illustration of an inspection device in a plan view.

FIG. 1 shows an inspection apparatus (full-bottle inspector) for the inspection of bottles 2 which are made of a transparent material, for example glass or a transparent plastic such as PET, for example, and are filled with a transparent liquid (e.g. beer, table water, mineral water, wine etc.). The bottles are inspected for the presence of any solid or foreign objects that may be present in the bottled liquid, and in one possible embodiment optically by imaging and image processing or analysis with an appropriate imaging and image processing system using opto-electrical sensors.

The bottles 2 to be inspected are delivered to the inspection apparatus 1 standing upright, i.e. with their bottle axis oriented in the vertical direction, by means of an external conveyor which is in the form of a conveyor belt 3.

The bottles 2 to be inspected thereby travel via a bottle inlet 6 formed by a spacer worm gear 4 and an inlet star wheel 5 on a transport system 7 of the inspection apparatus 1, with which the bottles 2 are moved to an inspection section of said apparatus. After the inspection, the bottles 2 are transferred via a transport star wheel 9 that forms a bottle outlet 8 back to the conveyor belt 3, on which the bottles 2 are transported away standing upright. Any bottles 2 in which foreign objects were found during the inspection are selected outward in a suitable manner on the conveyor belt 3.

In the illustrated possible embodiment, the transport system 7 comprises a horizontal guide 10, which is oval when viewed from overhead, on which a plurality of slides 11 that are movable in a direction of transport A are provided along the guide 10. Each slide 11 has a gripper 12 for the gripping or holding of an individual bottle 2 in the vicinity of its bottle mouth 2.1 which is closed with a cap 13, so that each bottle held by a gripper 12, suspended on this gripper, is moved with the transport system 7 along the inspection line. Each gripper 12 can be raised and lowered, e.g. by corresponding control cams, for the raising and lowering of the bottles 2 by a specified distance, as indicated by the double arrow B in FIG. 2, and can simultaneously or substantially simultaneously be pivoted around a horizontal axis 21.1, and in one possible embodiment in the illustrated embodiment around a horizontal axis parallel or virtually parallel to the direction of transport A, as indicated in FIG. 3 with the double arrow C.

For the movement of the slides 11 and the grippers 12 provided on them along the closed oval movement path formed by the guide 10, the slides 11 are connected with a common flexible element, such as a toothed belt 14, for example, which is guided by means of two toothed belt sprocket wheels 15 and 16 in the form of a closed loop which runs parallel or substantially parallel to the guide 10 and is located in a horizontal plane, whereby one of the toothed belt sprocket wheels, namely for example the sprocket wheel 16, is driven in synchronization with the transport star wheel 5 and 9 so that the slides 11 are moved along the guide 10 in the direction of transport A, and a smooth transfer of each bottle from the transport star wheel 5 to a gripper 12 and from a gripper 12 to the transport star wheel 9 is essentially guaranteed or promoted.

In the vicinity of the pulley or toothed belt sprocket wheel 16 for the toothed belt 14 that runs inside the guide 10, the bottle inlet 6 and the bottle outlet 8 are provided so that the greater part of the transport section of the transport system 7 is available as an inspection line.

On the transport or inspection line formed by the transport system 7, in the illustrated possible embodiment three optoelectrical sensors are provided in the form of individual cameras 17, 18 and 19, which are components of an imaging and image processing or analysis system which, in addition to the cameras 17 through 19, also has a computer-assisted electronic system 20 or an electronic system 20 formed by a computer for the image processing and/or analysis.

Figure 3A:
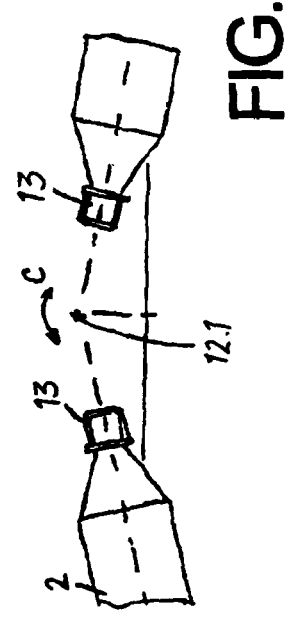
FIGS. 3A, 3B, 3C, 3D, and 3E display different steps in the method according to the present application for the inspection of bottles or similar containers made of a transparent material.
Figure 3B:
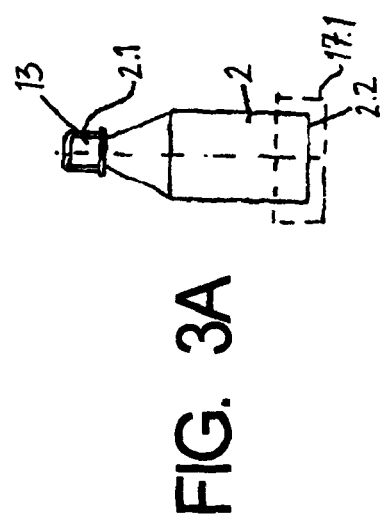

The steps of the method of the inspection method performed with the inspection apparatus 1 are illustrated in FIGS. 3A, 3B, 3C, 3D, and 3E. The bottles 2 that are delivered via the conveyor belt 3 or the external conveyor are each picked up at the container inlet 6 by a gripper 12 and are moved past the first camera oriented with their bottle axes still in the vertical or substantially vertical direction, whereby the first camera generates a first image or reference image of the respective bottle 2 (FIG. 3A). The camera 17 is thereby adjusted or oriented so that it generates an image of a very critical image area 17.1 of the respective bottle 2 which is potentially affected by foreign objects, i.e. an image area 17.1 which in one possible embodiment also includes the bottle bottom 2.2 which is opposite the cap 13, which experience indicates is the area in which solid or foreign objects, if they are any in a bottle 2, will primarily settle. As the respective bottle 2 continues to move with the transport system, there is then, for example, a "shaking" produced by multiple pivoting movements of the gripper 12 and thus also of the bottle 2 around the gripper pivoting axis 12.1, and in one possible embodiment out of the vertical orientation at an angle which can be, for example, up to eighty degrees or greater (e.g. up to one hundred degrees) to the left and to the right, to dislodge any foreign objects that may be present in the respective bottle 2 and may stick to the inside surface of the bottle 2 (FIG. 3B).

Figure 3C:
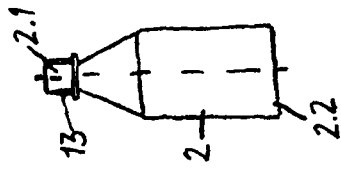

The respective bottle is then pivoted into an inclined position, so that the bottle axis is at an angle of less than ninety degrees with the vertical, which angle opens toward the bottom and the bottle points diagonally downward with its bottle 2.2 (FIG. 3C). In this position, any solid or foreign objects that may be present drop or are deposited in the angular area formed between the bottle bottom and the peripheral wall of the bottle 2, each bottle 2 is moved past the camera 18 to generate an additional image or a first inspection image. The camera 18 is set so that it images an area 18.1 of the respective bottle 17.1. On account of the pivoted position of the bottles 2 as they move past the camera 18, the image area 18.1 is correspondingly rotated with reference to the respective bottle or its axis, but remain identical with the image area 17.1. The rotation of the image area 18.1 can be compensated during the image processing by software, for example. It should be understood that it is not necessary for the solid or foreign objects to be deposited in the angular area formed between the bottle bottom and the peripheral wall of the bottle 2 in order to permit detection thereof. Essentially any object that moves or changes in position from one image to the next, regardless of the position of the object in the bottle or container at the time the image is obtained, will be detected as being a foreign object based on its change of position, as opposed to, for example, a scratch or other defect in the container or bottle, which would not change in position from one image to the next.

Figure 3D:
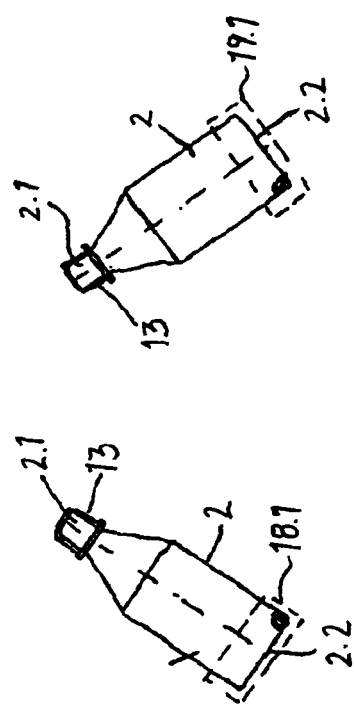
Figure 3E:
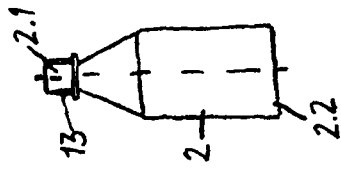

Then the respective bottle is pivoted into a diagonal position which is opposite to the diagonal position seen in FIG. 3C, so that the bottle axis again forms an angle of less than ninety degrees with the vertical, whereby the angle is open toward the bottom, and the bottle points diagonally downward with its bottom 2.2 (FIG. 3D). In this position, each bottle 2 is moved past the camera 19 for the generation of an additional image or of a second inspection image. The camera 19 is also set so that it images an area 19.1 of the respective bottle 2, which is in turn identical with the image area 17.1. On account of the pivoted position of the bottles 2 being moved past the camera 19, the image area 19.1 is correspondingly rotated, with reference to the respective bottle or its axis, but is identical with the image area 17.1 so that images of identical image areas 17.1, 18.1 and 19.1 are available for the analysis.

From the comparison of the images generated by the cameras 17, 18 and 19, the electronic system 20 analyzes each bottle 2 with reference to any solid or foreign objects that may be present in the bottle. The analysis method, which is based on a comparison of the images, utilizes the knowledge that at least some of the solid bodies that may be present in a bottle, in one possible embodiment after the pivoting or shaking (FIG. 3B), will be in a different position in the second and/or third image generated by the camera 18 or 19 respectively, than in the image generated by the camera 17, while on the other hand defects in the respective bottle 2, e.g. bubbles, inclusions, scratches, seams, etc. in or on the wall of the bottle will be practically identical in form and position in the images from the cameras 17 through 19 and can be disregarded in the image processing or analysis as characteristics which are unimportant for the image processing or analysis. In this embodiment of the present application, for the two inspection images the respective bottle 2 is pivoted around a single axis which is the optical axis of the cameras 17 through 19 or is oriented parallel or virtually parallel to their optical axes, and runs, for example, perpendicular or substantially perpendicular or radial bottle axis.

After passing the camera 19, each bottle 2 is pivoted back into its vertical position (FIG. 3E) and is transferred via the bottle outlet 8 to the external conveyor or to the external conveyor belt 3.

In other words, in at least one possible embodiment, an image is obtained by a sensor 17, such as a camera or other sensor described herein, which has been oriented and positioned to obtain an image of a section of the bottle or container, that is, a first image area 17.1. The image obtained by sensor 17 is transmitted to and stored in an electronic system 20, such as a computer system. The container is subsequently pivoted around an axis which runs substantially perpendicular to a central longitudinal axis of the container such that the container is no longer in a vertical position, but rather is tilted at an angle to the vertical position. An image is then obtained by a sensor 18, which has also been oriented and positioned to obtain an image of a section of the bottle or container, that is, a second image area 18.1. The section of the bottle or container of which the sensor 18 obtains an image is the same section of the bottle or container of which the sensor 17 obtains an image. The image obtained by sensor 18 is transmitted to and stored in the electronic system 20. In at least one possible embodiment, only the two sensors 17, 18 are utilized. After the images have been obtained by the two sensors 17, 18, the image of obtaining by sensor 18 is compared with the image obtained by sensor 17 to determine if an object present in the first image changes or shifts in position in the second image. In this manner, foreign objects, solid contaminants, or other objects or contaminants which are visible to the eye of a consumer or other person viewing the product in the bottle or container, can be detected. In at least one other possible embodiment, a third sensor 19 may be utilized to obtain yet another image of an image area 19.1, which image area 19.1 covers the same section of the container or bottle as the other image areas 17.1 and 18.1. In such an embodiment, the bottle or container could be pivoted or swung back around the axis to another position in which the container is again tilted at an angle with respect to the original vertical position of the bottle or container. The image of the image area 19.1 could then be compared with either or both of the images of the image areas 17.1 and 18.1. This additional analysis of a third image area 19.1 could further enhance the accuracy and detection of undesirable or foreign objects in the liquid product in the container or bottle by subjecting the objects to additional movement inside the liquid. Finally, in at least one other possible embodiment, subsequent to the obtaining of the image of the first image area 17.1 and prior to the obtaining of the image of the second image area 18.1 and/or the third image area 19.1, the container or bottle may be pivoted or swung about the axis and out of its vertical position at least one or two times to a position nearly perpendicular to the vertical position, i.e. nearly horizontal or on its side. This pivoting or swinging of the container or bottle could be utilized to forcefully dislodge undesirable or foreign objects that may be stuck to, or may be slightly adhering to, an interior surface of the container or bottle, or at least encourage movement of the objects inside the liquid in the container or bottle for easier detection by the sensors 18 and/or 19. In at least one possible embodiment, at least one or all of the pivoting or swinging movements of the container or bottle are performed at a speed sufficient to cause the objects to move a distance sufficient to permit detection of a change or shift in the position of the objects in the bottle or container by the sensors 18, 19.

The image areas 17.1, 18.1 and 19.1 are thereby selected, for example, so that in the direction radial to the bottle axis they each comprise an area that includes the total bottle diameter and in the direction of the bottle axis an area of approximately thirty to thirty-five millimeters above the bottle bottom 2.2. To achieve a high quality during the inspection, the cameras 17, 18 and 19 are selected so that they have a camera or image resolution of at least 0.15 millimeter per pixel or greater, so that any solid or foreign objects with a size of 0.5×0.5×0.5 millimeters in transparent liquids housed in the bottles 6 can be detected and so that the error rate during the inspection is a maximum of 0.5 to one percent.

In at least one possible embodiment according to the present application, the dimensions of the solid or foreign objects to be detected may vary due to the type of liquid in the containers, the color of the liquid in the containers, and/or the consistency or viscosity of the liquid in the containers. For example, solid or foreign objects of a size dimensionally smaller than substantially about 0.5×0.5×0.5 millimeters may possibly be visually detectable by a consumer in liquids such as distilled water, sparkling water, flavored water, and/or ginger ale. However, in liquids having a darker color, a thicker consistency, and/or a higher viscosity, such as cola, wheat/white beer, and juices, among others, objects of smaller sizes may possibly not be as visually detectable by a consumer as objects of larger sizes. In other words, an object of about 0.5×0.5×0.5 millimeters or smaller may possibly be more visually detectable by a consumer in, for example, water, than in, for example, wheat beer. Thus, depending on the product being bottled, the inspection apparatus or system could be designed to detect objects that are dimensionally smaller or larger than 0.5×0.5×0.5 millimeters.

The image can be analyzed, for example, so that foreign objects are determined to be present if the evaluation of the image from the camera 18 and from the camera 19 show foreign objects (AND function) and/or if the image from camera 18 or from camera 19 shows foreign objects (OR function).

Additional embodiments of the inspection apparatus 1 show, for example, that the slides 11 are guided with rollers on the guide 10 and that the sled guide 10 is realized so that it is self-cleaning, does not require and/or desire oil, does not require and/or desire lubrication and is not sensitive to dirt, in one possible embodiment including the fact that any dirt or contamination caused by the system and/or by any broken bottles 2 cannot get into the guide. As a result of the pivoting of the grippers 12 around axes 12.1 parallel or substantially parallel to the direction of transport A, it is essentially guaranteed or promoted that it is possible for the grippers 12 to pivot even with a very tight sequence of the slides 11 in the direction of transport A. The cameras 17, 18 and 19 are each offset laterally with respect to the slide guide 10 when seen in a plan view of the inspection apparatus 1, and in one possible embodiment the cameras 17 and 19 are outside the loop formed by the slide guide 10 and the camera 18 is inside this loop. Each camera 17, 18 and 19 is therefore associated with an appropriate lighting device.

Figure 4:
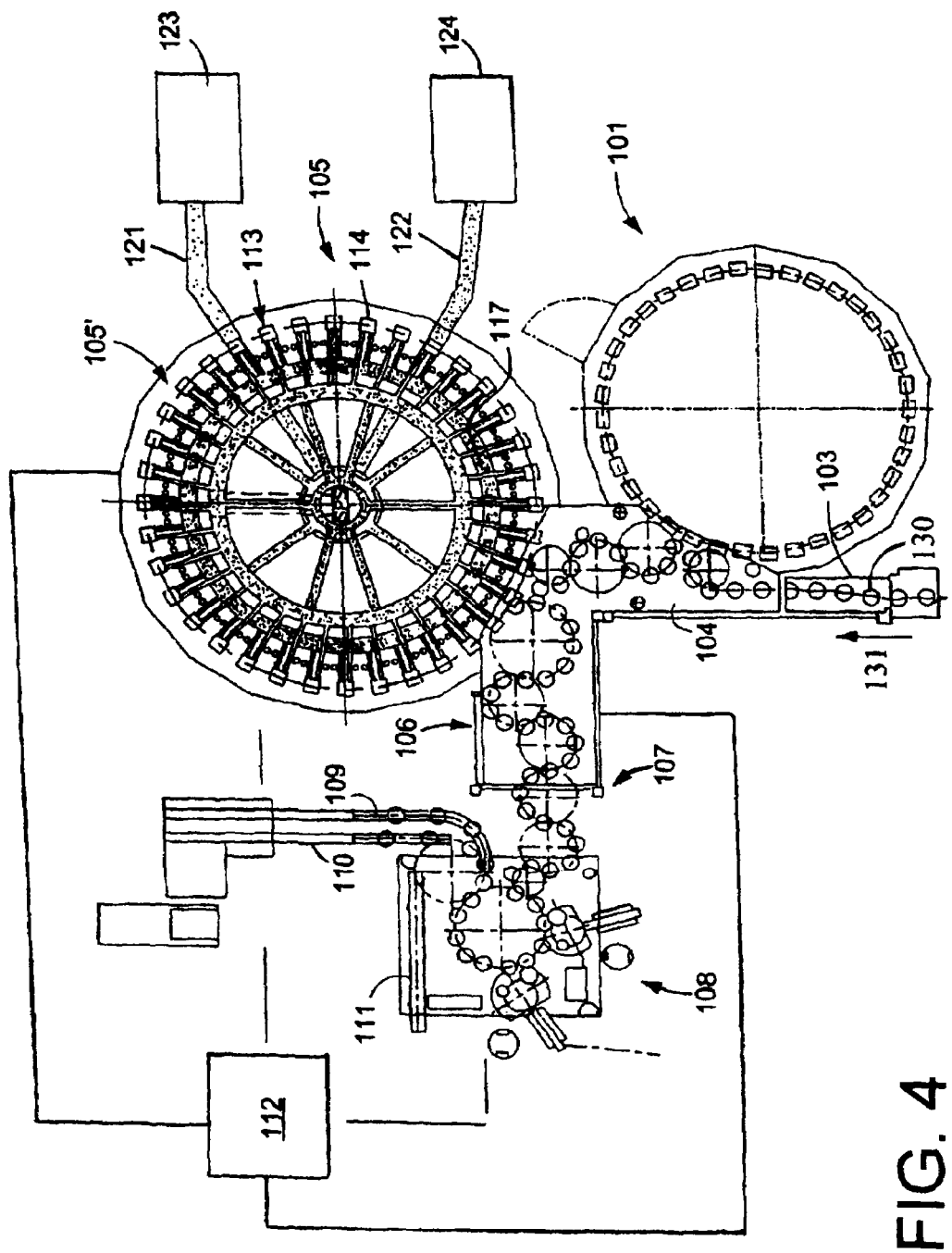
FIG. 4 shows schematically the main components of one possible embodiment example of a system for filling containers, for example a beverage bottling plant for filling bottles with at least one liquid beverage, in accordance with at least one possible embodiment, in which system or plant could possibly be utilized at least one aspect, or several aspects, of the embodiments disclosed herein.

FIG. 4 shows schematically the main components of one possible embodiment example of a system for filling containers, specifically, a beverage bottling plant for filling bottles 130 with at least one liquid beverage, in accordance with at least one possible embodiment, in which system or plant could possibly be utilized at least one aspect, or several aspects, of the embodiments disclosed herein.

FIG. 4 shows a rinsing arrangement or rinsing station 101, to which the containers, namely bottles 130, are fed in the direction of travel as indicated by the arrow 131, by a first conveyer arrangement 103, which can be a linear conveyor or a combination of a linear conveyor and a starwheel. Downstream of the rinsing arrangement or rinsing station 101, in the direction of travel as indicated by the arrow 131, the rinsed bottles 130 are transported to a beverage filling machine 105 by a second conveyer arrangement 104 that is formed, for example, by one or more starwheels that introduce bottles 130 into the beverage filling machine 105.

The beverage filling machine 105 shown is of a revolving or rotary design, with a rotor 105', which revolves around a central, vertical machine axis. The rotor 105' is designed to receive and hold the bottles 130 for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles 130 to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 4, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individually-controllable fluid or control valves, so that in each bottle 130, the first product or the second product can be filled by means of an appropriate control of the filling product or fluid valves.

Downstream of the beverage filling machine 105, in the direction of travel of the bottles 130, there can be a beverage bottle closing arrangement or closing station 106 which closes or caps the bottles 130. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles 130. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles 130 to different locations.

The first output conveyer arrangement 109, in the embodiment shown, is designed to convey bottles 130 that are filled with a first type of liquid beverage supplied by, for example, the supply reservoir 123. The second output conveyer arrangement 110, in the embodiment shown, is designed to convey bottles 130 that are filled with a second type of liquid beverage supplied by, for example, the supply reservoir 124. The third output conveyer arrangement 111, in the embodiment shown, is designed to convey incorrectly labeled bottles 130. To further explain, the labeling arrangement 108 can comprise at least one beverage bottle inspection or monitoring device that inspects or monitors the location of labels on the bottles 130 to determine if the labels have been correctly placed or aligned on the bottles 130. The third output conveyer arrangement 111 removes any bottles 130 which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

The present application was described above on the basis of one possible embodiment. It goes without saying that numerous modifications and variations are possible without thereby going beyond the teaching of the present application. Therefore it is possible, for example, in a variation of the method described above, to omit the shaking or pivoting of the bottles 2 as illustrated in FIG. 3B and/or instead of three cameras to provide two cameras, for example the cameras 17 and 19, of which the camera 17 is again used for the generation of the reference image and the camera 19 for the actual imaging of foreign matter or foreign objects in the filled bottles 2, i.e. for the generation of the inspection image.

The present application was explained above on the assumption that exclusively transparent containers filled with transparent liquids are to be inspected with the present application. However, the present application is not limited to such applications. Instead, the inspection of non-transparent or translucent containers and/or the inspection of non-transparent or translucent liquids also falls within the scope of protection of the present application.

Because in such applications the inspection devices described above which operate using optical methods do not provide reliable results, the present application teaches methods which are able to penetrate and image non-transparent or non-translucent elements. These methods, for example, can be those that work with transmitters for radiation in the range of infrared radiation and/or with X-ray radiation. As the receiver elements which are ultimately used for the generation of an image of the object to be inspected that can be analyzed in the desired manner, it is possible, for example, to provide surface matrix sensors for electromagnetic radiation.

An additional embodiment of the inspection apparatus 1 is also that the ramp 21 of the inspection apparatus 1 that forms the bottle inlet 6 and the bottle outlet 8 and has the corresponding elements is realized so that the spacer and divider worm gear 4 and the two transport star wheels can be removed and/or bypassed, so that the bottles 2 on the conveyor belt 3 or on the external conveyor formed by this conveyor belt can be transported past the inspection apparatus, i.e. a plant that has the inspection apparatus 1 can also be operated without the inspection apparatus 1 or bypassing the inspection apparatus 1 practically without any setup times.

An additional embodiment of the present application shows that an inspection apparatus was realized in which the bottles 2 are held on flexible elements such as toothed belts 14, for example, and are moved past the inspection stations in an essentially linear motion. As a result of this method, the inspection apparatus according to the present application can be adapted to the local layout with little construction effort. The treatment line and thus also the treatment or inspection time can also be lengthened or shortened as desired. In addition, almost as many treatment or inspection stations as desired can be located in the treatment line.

The present application also teaches that the guide 10 of the flexible element, at least in subsections, is curved and/or circular and/or arced and/or in a straight line, so that the treatment line can be quickly and economically adapted to the specific requirements.

Method for the inspection of bottles or similar containers filled with a liquid, whereby the containers are inspected with an opto-electrical and/or electromagnetic imaging and processing or analysis system for any foreign objects that may be present in the bottled liquid, and in one possible embodiment on the basis of images from an opto-electrical and/or electromagnetic sensor system.

One feature or aspect of an embodiment is believed at the time of the filing of this patent application to possibly reside broadly in a method for the inspection of bottles or similar containers 2 filled with a pourable liquid being bottled, whereby the containers 2 are inspected with an opto-electrical or electromagnetic imaging and processing or analysis system 17, 18, 19, 20 to detect any solid or foreign objects that may be housed in the pourable liquid being bottled, wherein a reference image is generated of each container 2 in a first container orientation with an opto-electrical or electromagnetic sensor 17, that then at least one additional image of each container 2 is generated in at least one additional orientation which differs from the first container orientation with the opto-electrical or electromagnetic sensor 18, 19, and that the inspection for potential foreign objects is performed by processing and/or comparison of the reference image with the at least one additional image.

Another feature or aspect of an embodiment is believed at the time of the filing of this patent application to possibly reside broadly in the method, wherein the containers 2 are made of a transparent or translucent material, and/or that the liquid being bottled is transparent or translucent.

Yet another feature or aspect of an embodiment is believed at the time of the filing of this patent application to possibly reside broadly in the method, wherein the containers 2 are not made of a transparent or translucent material, and/or that the bottled liquid is not transparent or translucent.

Still another feature or aspect of an embodiment is believed at the time of the filing of this patent application to possibly reside broadly in the method, wherein the reference image and the at least one additional image are generated chronologically one after the other with different opto-electrical or electromagnet sensors 17, 18, 19.

A further feature or aspect of an embodiment is believed at the time of the filing of this patent application to possibly reside broadly in the method, wherein after the reference image, in chronological sequence one after another, at least two additional images are generated in container orientations that are different from each other and from the first container orientation.

Another feature or aspect of an embodiment is believed at the time of the filing of this patent application to possibly reside broadly in the method, wherein the containers 2 are each oriented with the container bottom downward during the generation of the images.

Yet another feature or aspect of an embodiment is believed at the time of the filing of this patent application to possibly reside broadly in the method, wherein the container orientation is varied during the generation of the images, that the image plane of the respective imaged container area 17.1, 18.1, 19.1 is identical or essentially identical in the processed or compared images or in images derived from them for the processing.

Still another feature or aspect of an embodiment is believed at the time of the filing of this patent application to possibly reside broadly in the method, wherein the different container orientation during the generation of the images is achieved by pivoting the container 2 in question around an axis 12.1 which is parallel or essentially parallel to the optical axis of the opto-electrical sensors 17, 18, 19.

A further feature or aspect of an embodiment is believed at the time of the filing of this patent application to possibly reside broadly in the method, wherein to vary the container orientation, the containers 2 are pivoted around an axis which is radial to the container axis.

Another feature or aspect of an embodiment is believed at the time of the filing of this patent application to possibly reside broadly in the method, wherein between the generation of two images, the container 2 is shaken, in one possible embodiment by being pivoted once or twice.

Yet another feature or aspect of an embodiment is believed at the time of the filing of this patent application to possibly reside broadly in the method, wherein optical scanners and/or cameras 17, 18, 19 or camera systems are used as opto-electrical sensors.

Still another feature or aspect of an embodiment is believed at the time of the filing of this patent application to possibly reside broadly in the method, wherein surface matrix sensors for electromagnetic radiation 17, 18, 19 are used as electromagnetic sensors.

A further feature or aspect of an embodiment is believed at the time of the filing of this patent application to possibly reside broadly in the method, wherein during the image analysis, image elements that are identical or essentially identical in shape and/or position in the images are eliminated as elements that are not essential for the inspection and/or are not taken into consideration.

One feature or aspect of an embodiment is believed at the time of the filing of this patent application to possibly reside broadly in the method, wherein the presence of foreign objects is determined when the analysis of at least two images shows at least one foreign object.

Another feature or aspect of an embodiment is believed at the time of the filing of this patent application to possibly reside broadly in the method, wherein the presence of foreign objects is determined already if the analysis of at least one image shows at least one foreign object.

Yet another feature or aspect of an embodiment is believed at the time of the filing of this patent application to possibly reside broadly in the method, wherein an image, e.g. a reference image, is generated with the containers 2 oriented with the container axis in the vertical direction.

Still another feature or aspect of an embodiment is believed at the time of the filing of this patent application to possibly reside broadly in the method, wherein the additional images are produced with containers 2 inclined with their container axis at an angle with respect to the vertical.

A further feature or aspect of an embodiment is believed at the time of the filing of this patent application to possibly reside broadly in the method, wherein the image area 17.1, 18.1, 19.1 imaged by the opto-electrical sensors 17, 18, 19 is identical our essentially identical.

Another feature or aspect of an embodiment is believed at the time of the filing of this patent application to possibly reside broadly in the method, wherein for the inspection, the containers 2 are moved past the opto-electrical sensors 17, 18, 19 with a transport system 7.

Yet another feature or aspect of an embodiment is believed at the time of the filing of this patent application to possibly reside broadly in the method, wherein the containers 2 are held suspended on the transport system 7 or on grippers 12 on the transport system.

Still another feature or aspect of an embodiment is believed at the time of the filing of this patent application to possibly reside broadly in the method, wherein the containers 2, to vary their orientation, are pivoted around an axis parallel or virtually parallel to the direction of transport A of the transport system 7.

A further feature or aspect of an embodiment is believed at the time of the filing of this patent application to possibly reside broadly in an apparatus for the inspection of bottles or similar containers 2 filled with a liquid, with an opto-electrical or electromagnetic imaging and processing or analysis system 17, 18, 19, 20 for the detection of any solid matter or foreign objects that may be present in the bottled liquid, comprising an opto-electrical or electromagnetic sensor system 17, 18, 19 with which, in a first container orientation, a reference image of each container 2 is generated, and then in at least one additional container orientation that varies from the first orientation, at least one additional image is generated, and by an electronic system 20 for the analysis of the images for the monitoring for possible foreign objects.

Another feature or aspect of an embodiment is believed at the time of the filing of this patent application to possibly reside broadly in the apparatus, wherein the opto-electrical sensor system has a plurality of opto-electrical sensors 17, 18, 19 along an inspection line on which the containers 2 are moved for the generation of the reference image and of the at least one additional image.

Yet another feature or aspect of an embodiment is believed at the time of the filing of this patent application to possibly reside broadly in the apparatus, wherein the opto-electrical sensor system has at least three opto-electrical sensors 17, 18, 19 located along an inspection line.

Still another feature or aspect of an embodiment is believed at the time of the filing of this patent application to possibly reside broadly in the apparatus, comprising a transport system 7 with which the containers 2 are moved past the opto-electrical sensors 17, 18, 19 on the inspection line.

A further feature or aspect of an embodiment is believed at the time of the filing of this patent application to possibly reside broadly in the apparatus, wherein the containers 2 are held in a suspended position on the transport system 7 or on grippers 12 which are located on the transport system.

One feature or aspect of an embodiment is believed at the time of the filing of this patent application to possibly reside broadly in the apparatus, wherein the containers 2 are held on the transport system 7 so that they can be pivoted to vary their orientation.

Another feature or aspect of an embodiment is believed at the time of the filing of this patent application to possibly reside broadly in the apparatus, wherein the containers 2 are held on the transport system 7 so that they can be pivoted around an axis parallel or substantially parallel to the direction of transport A to vary their orientation.

Yet another feature or aspect of an embodiment is believed at the time of the filing of this patent application to possibly reside broadly in the apparatus, wherein the opto-electrical sensors are optical scanners and/or cameras 17, 18, 19 or camera systems.

Still another feature or aspect of an embodiment is believed at the time of the filing of this patent application to possibly reside broadly in the apparatus, comprising a ramp 21 which forms a container inlet 6 and a container outlet 8 of the transport system 7, which ramp is connected to an external conveyor 3 for the delivery and removal of the containers 2, whereby the ramp 21 can be retooled to make the containers 2 bypass the inspection line on the external conveyor 3.

A further feature or aspect of an embodiment is believed at the time of the filing of this patent application to possibly reside broadly in the apparatus, wherein the ramp 21 can be retooled by removing the functional elements 4, 5; 9 that form the container inlet 6 and the container outlet 8 so that the containers 2 by pass the inspection line.

Another feature or aspect of an embodiment is believed at the time of the filing of this patent application to possibly reside broadly in an inspection apparatus for the inspection of containers, whereby the containers are held by a holding device and are moved along a treatment or inspection line by means of a linear movement, whereby the containers 2 are guided along at least one inspection station, wherein within the inspection apparatus a flexible element is provided on which the containers 2 are held and by means of which the containers 2 are moved along the treatment line.

Yet another feature or aspect of an embodiment is believed at the time of the filing of this patent application to possibly reside broadly in the inspection apparatus, wherein the flexible element is a toothed belt 14.

Still another feature or aspect of an embodiment is believed at the time of the filing of this patent application to possibly reside broadly in the inspection apparatus, wherein the flexible element is held on a guide 10.

A further feature or aspect of an embodiment is believed at the time of the filing of this patent application to possibly reside broadly in the inspection apparatus, wherein the guide 10, at least in sections, is curved and/or circular and/or arc-shaped and/or straight.

Another feature or aspect of an embodiment is believed at the time of the filing of this patent application to possibly reside broadly in the inspection apparatus, wherein at least one pulley is provided for the flexible element.

Yet another feature or aspect of an embodiment is believed at the time of the filing of this patent application to possibly reside broadly in the inspection apparatus, wherein the at least one pulley is a toothed belt sprocket wheel.

Still another feature or aspect of an embodiment is believed at the time of the filing of this patent application to possibly reside broadly in an apparatus for the inspection of bottles or similar containers 2 filled with a liquid, with an opto-electrical or electromagnetic imaging and processing or analysis system 17, 18, 19, 20 for the imaging of any solid matter or foreign objects that may be present in the bottled liquid, and with a transport system 7, with which the containers 2 are moved for the inspection on a transport or inspection line, and with a ramp 21 that forms a container inlet 6 and a container outlet 8 of the transport system 7, which ramp is connected to an external conveyor 3 for the delivery and removal of the containers, wherein the ramp 21 can be modified so that the containers 2 are transported past the inspection line on the external conveyor 3.

A further feature or aspect of an embodiment is believed at the time of the filing of this patent application to possibly reside broadly in the apparatus, wherein the ramp 21 can be retooled by removal of the functional elements 4, 5; 9 that form the container inlet 6 and the container outlet 8 to transport the containers 2 past the inspection line.

One feature or aspect of an embodiment is believed at the time of the filing of this patent application to possibly reside broadly in the apparatus, wherein the ramp 21 can be switched by moving elements from a first position into a second position, thereby avoiding the need and/or desire for the installation or removal of elements, for the mode in which the containers 2 bypass the inspection line.

Another feature or aspect of an embodiment is believed at the time of the filing of this patent application to possibly reside broadly in a method for the inspection of bottles or similar containers 2 filled with a pourable liquid being bottled, whereby the containers 2 are inspected with an opto-electrical or electromagnetic imaging and processing or analysis system 17, 18, 19, 20 to detect any solid or foreign objects that may be housed in the pourable liquid being bottled, whereby a reference image is generated of each container 2 in a first container orientation with an opto-electrical or electromagnetic sensor 17, then at least one additional image of each container 2 is generated with an opto-electrical of electromagnetic sensor 18, 19, and the inspection for potential foreign objects is performed by processing and/or comparison of the reference image with the at least one additional image, wherein the at least one additional image is generated in at least one additional container orientation which differs from the first container orientation.

Yet another feature or aspect of an embodiment is believed at the time of the filing of this patent application to possibly reside broadly in the method, wherein the container orientation is varied by pivoting the containers 2.

Still another feature or aspect of an embodiment is believed at the time of the filing of this patent application to possibly reside broadly in the method, wherein to vary the container orientation, the containers 2 are pivoted around an axis which is radial to the container axis.

A further feature or aspect of an embodiment is believed at the time of the filing of this patent application to possibly reside broadly in the method, wherein between the generation of two images, the container 2 is shaken, preferably by being pivoted one or more times.

Another feature or aspect of an embodiment is believed at the time of the filing of this patent application to possibly reside broadly in the inspection apparatus for the inspection of bottles or similar containers 2 filled with a liquid, with an opto-electrical or electromagnetic imaging and processing or analysis system 17, 18, 19, 20 for the detection of any solid matter or foreign objects that may be present in the bottled liquid, with an opto-electrical or electromagnetic sensor system 17, 18, 19 with which, in a first container orientation, a reference image of each container 2 is generated, and then at least one additional image is generated, and with an electronic system 20 for the analysis of the images for the monitoring for possible foreign objects, wherein the transport system is realized so that it can pivot the containers 2 to generate the at least one additional image in an additional container orientation that differs from the first container orientation.

Yet another feature or aspect of an embodiment is believed at the time of the filing of this patent application to possibly reside broadly in the inspection apparatus for the inspection of containers, whereby the containers are moved in a linear movement along a treatment or inspection line to at least one inspection station, and whereby within the inspection apparatus a flexible element is provided on which the containers 2 are held and by means of which the containers 2 are moved along the treatment line, wherein the flexible element is provided with grippers 12 that act as a holding device for the containers 2.

The components disclosed in the various publications, disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications and publications recited herein, and in the Declaration attached hereto, are hereby incorporated by reference as if set forth in their entirety herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

All of the patents, patent applications or patent publications, which were cited in the International Search Report dated Sep. 10, 2008, and/or cited elsewhere are hereby incorporated by reference as if set forth in their entirety herein as follows: U.S. Pat. No. 4,136,930, having the title "METHOD AND APPARATUS FOR DETECTING FOREIGN PARTICLES IN FULL BEVERAGE CONTAINERS," published on Jan. 30, 1979; WO 01/44791, having the title "APPARATUS FOR NON-DESTRUCTIVE INSPECTION OF CYLINDRICAL CONTAINERS FOR LIQUID PRODUCTS," published on Jun. 21, 2001; U.S. Pat. No. 4,605,851, having the title "PROCESS AND DEVICE FOR DETECTING FOREIGN BODIES IN A LIQUID," published on Aug. 12, 1986; WO 96/18883, having the title "A METHOD AND AN APPARATUS FOR IDENTIFYING FOREIGN BODIES IN PACKAGED BEVERAGES, AS WELL AS USE OF THE APPARATUS," published on Jun. 20, 1996; FR 2,746, 502, having the following English translation of the French title "DETECTING GLASS FRAGMENTS IN GLASS CONTAINERS," published on Sep. 26, 1997; EP 1,493,690, having the title "BELT DRIVE ASSEMBLY FOR CONTAINER INSPECTION MACHINE," published on Jan. 5, 2005; U.S. Pat. No. 5,492,216, having the title "METHOD AND APPARATUS FOR TRANSFERRING CONTAINERS WHILE MAINTAINING VERTICAL ORIENTATION," published on Feb. 20, 1996; U.S. Pat. No. 3,557,950, having the title "PHOTO-ELECTRIC CRACK DETECTOR FOR GLASS BOTTLES," published on Jan. 26, 1971; U.S. Pat. No. 5,926,268, having the title, "SYSTEM AND METHOD FOR STRESS DETECTION IN A MOLDED CONTAINER," published on Jul. 20, 1999; U.S. Pat. No. 4,209,802, having the title "GLASS FRAGMENT DETECTOR," published on Jun. 24, 1980; US 2005/263443, having the title "METHOD AND APPARATUS FOR INSPECTING CONTAINERS," published on Dec. 1, 2005; U.S. Pat. No. 5,917,602, having the title "SYSTEM AND METHOD FOR IMAGE ACQUISITION FOR INSPECTION OF ARTICLES ON A MOVING CONVEYOR," published on Jun. 29, 1999; U.S. Pat. No. 4,801,319, having the title "APPARATUS AND ASSOCIATED METHOD FOR CONTAINER SAMPLING FOR INSPECTION," published on Jan. 31, 1989; and EP 1,700,643, having the following English translation of the German title "DEVICE FOR FEEDING CONTAINERS," published on Sep. 13, 2006.

All of the patents, patent applications or patent publications, which were cited in the German Office Action dated Nov. 30, 2007, and/or cited elsewhere are hereby incorporated by reference as if set forth in their entirety herein as follows: DE 10 2004 051 961, having the following English translation of the German title "DEVICE FOR INSPECTING FOREIGN BODIES IN FILLED CONTAINER COMPRISES VIBRATION UNIT FOR VIBRATING CONTAINER," published on May 4, 2006; EP 0 277 629, having the following English translation of the German title "METHOD AND DEVICE FOR DETECTING IMPURITIES IN FLUIDS," published on Aug. 10, 1988; and DE 299 19 761, having the following German title "INSPEKTIONSMASCHINE," published on Dec. 21, 2000.

Some examples of cameras or the like optical monitoring apparatus that may possibly be utilized or possibly adapted for use in at least one possible embodiment of the present application may possibly be found in the following U.S. Pat. No. 5,233,186 issued to Ringlien on Aug. 3, 1993; No. 5,243,400 issued to Ringlien on Sep. 7, 1993; No. 5,369,713 issued to Schwartz et al. on Nov. 29, 1994; No. 5,442,446 issued to Gerber et al. on Aug. 15, 1995; No. 5,661,295 issued to Buchmann et al. on Aug. 26, 1997; and No. 5,898,169 issued to Nodbryhn on Apr. 27, 1999.

Some examples of worm gears used in high speed bottling plants that may possibly be utilized or possibly adapted for use in at least one possible embodiment of the present application may possibly be found in the following U.S. Pat. No. 7,331,156 issued to Hartness et al. on Feb. 19, 2008; and No. 6,276,113 issued to Bernhard on Aug. 21, 2001.

Some examples of optical, opto-electric, infrared, X-ray, and electromagnetic sensors for use in inspecting the contents of containers for contaminants that may possibly be utilized or possibly adapted for use in at least one possible embodiment of the present application may possibly be found in the following U.S. Pat. No. 5,067,616 issued to Plester et al. on Nov. 26, 1991; No. 7,453,980 issued to Gilevich et al. on Nov. 18, 2008; No. 7,480,040 issued to Juvinall et al. on Jan. 20, 2009; No. 7,385,174 issued to Ringlien on Jun. 10, 2008; No. 7,126,686 issued to Tsujita on Oct. 24, 2006; and No. 7,010,863 issued to Juvinall et al. on Mar. 14, 2006.

Some examples of cameras with high shutter speeds, which may possibly be utilized or adapted for use in at least one possible embodiment of the present application, may possibly include, among others: ELMO 9754 micro camera MN400 one-piece resolution color micro camera, manufactured by ELMO Co.; Hitachi KP-FD202 PCL PcCL camera, manufactured by Hitachi Kokusai Electric America, Ltd; High Speed Dome camera MVT-HO52/18S, manufactured by Mvteam Industrial Limited; and Zoom Camera AC-822H, manufactured by Shenzhen Jixinjie Electronic Co., Ltd.

Some examples of cameras with high image resolutions, which may possibly be utilized or adapted for use in at least one possible embodiment of the present application, may possibly include, among others: the Specialised Imaging SIR2 camera, manufactured by Specialised Imagining Ltd; Lw11059 camera, manufactured by Lumenera Corporation; High Speed and Resolution 2048 to 8196 Pixel Line Scan Camera, sold by Hill Technical Sales Corp.; and Fixed PoE Network Camera VB-C50FSi, manufactured by Canon U.S.A., Inc.

Some examples of ultrasonic sensors, which may possibly be utilized or adapted for use in at least one possible embodiment according to the present application, may possibly be found in the following U.S. Pat. No. 7,317,663, having the title "ULTRASONIC SENSOR," published on Jan. 8, 2008; No. 7,525,237, having the title "ULTRASONIC SENSOR," published on Apr. 28, 2009; No. 7,497,121, having the title "ULTRASONIC SENSOR," published on Mar. 3, 2009; No. 7,522,475, having the title "ULTRASONIC SENSOR AND OBSTACLE DETECTION DEVICE," published on Apr. 21, 2009; No. 7,343,803, having the title "MODULAR ULTRASONIC SENSOR," published on Mar. 18, 2008; and No. 7,329,975, having the title "ULTRASONIC SENSOR," published on Feb. 12, 2008.

The patents, patent applications, and patent publication listed above in the preceding eight paragraphs are herein incorporated by reference as if set forth in their entirety. The purpose of incorporating U.S. patents, non-U.S. patents, publications, etc. is solely to provide additional information relating to technical features of one or more embodiments, which information may not be completely disclosed in the wording in the pages of this application. Words relating to the opinions and judgments of the author and not directly relating to the technical details of the description of the embodiments therein are not incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the above-mentioned words in this sentence, when not used to describe technical features of one or more embodiments, are not considered to be incorporated by reference herein.

The corresponding foreign and international patent publication applications, namely, Federal Republic of Germany Patent Application No. 10 2006 054 099.9, filed on Nov. 15, 2006, having inventors Volker TILL, Paul-Gerhard KAHLISCH, and Horst BdCKER, and DE-OS 10 2006 054 099.9 and DE-PS 10 2006 054 099.9, and International Application No. PCT/EP2007/009633, filed on Nov. 7, 2007, having WIPO Publication No. WO 2008/058658 and inventors Volker TILL, Paul-Gerhard KAHLISCH, and Horst BdCKER, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

The purpose of incorporating the corresponding foreign equivalent patent application(s), that is, PCT/EP2007/009633 and German Patent Application 10 2006 054 099.9, is solely for the purpose of providing a basis of correction of any wording in the pages of the present application, which may have been mistranslated or misinterpreted by the translator. Words relating to opinions and judgments of the author and not directly relating to the technical details of the description of the embodiments therein are not to be incorporated by reference. The words all, always, absolutely, consistently, preferably, guarantee, particularly, constantly, ensure, necessarily, immediately, endlessly, avoid, exactly, continually, expediently, need, must, only, perpetual, precise, perfect, require, requisite, simultaneous, total, unavoidable, and unnecessary, or words substantially equivalent to the abovementioned word in this sentence, when not used to describe technical features of one or more embodiments, are not generally considered to be incorporated by reference herein.

Statements made in the original foreign patent applications PCT/EP2007/009633 and DE 10 2006 054 099.9 from which this patent application claims priority which do not have to do with the correction of the translation in this patent application are not to be included in this patent application in the incorporation by reference.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72 (b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

AT LEAST PARTIAL NOMENCLATURE

1 Inspection apparatus (Full-bottle inspector)
2 Bottle
2.1 Bottle mouth
2.2 Bottle bottom
3 External conveyor or external conveyor belt
4 Spacer and divider worm gear
5 Transport star wheel
6 Bottle inlet
7 Transport system
8 Bottle outlet
9 Transport star wheel
10 Slide guide
11 Slide
12 Gripper
12.1 Pivoting axis of the gripper 12
13 Bottle cap
14 Toothed belt
15, 16 Toothed belt sprocket wheel
17, 18, 19 Camera
17.1, 18.1, 19.1 Image area
20 Electronic system
21 Ramp
A Direction of transport
B Direction of reciprocating motion
C Pivoting of the respective gripper 12

What is claimed is:

1. A method of inspecting liquid-filled containers, such as bottles and similar containers, said method comprising:
   generating a first image of a container with a first sensor upon said container being in a first orientation in which the longitudinal axis of said container is disposed at a first vectoral position with respect to the vertical;
   moving said container to a second orientation in which the longitudinal axis of said container is disposed at a second, different, vectoral position with respect to the vertical, wherein at least one of said first and second vectoral positions is such that the longitudinal axis of said container is at a non-zero angle with respect to the vertical;
   generating a second image of said container with a second sensor upon said container being in said second orientation; and processing and/or comparing said first image with said second image using a computer system to determine if at least one foreign object is present in the liquid.

2. The method according to claim 1, wherein said container is moved between orientations by pivoting, and said container is pivoted about an axis which is radial to the longitudinal axis of said container.

3. The method according to claim 2, wherein:
the container orientation is varied during the generation of the images so that the image plane of the respective imaged container area is identical or essentially identical in the processed or compared images or in images derived from them for the processing; and
the different container position during the generation of the images is achieved by pivoting the container in question around an axis which is parallel or essentially parallel to the optical axis of the sensors.

4. The method according to claim 3, wherein said method further comprises:
moving said container to a third orientation in which the longitudinal axis of said container is disposed at a third vectoral position with respect to the vertical different from said second vectoral position; and
generating a third image of said container with a third sensor upon said container being in said third orientation; and
one of (A) and (B):
(A) said first image and said second image are generated chronologically one after the other with opto-electrical sensors; and
the containers are made of a transparent or translucent material, and/or the liquid being bottled is transparent or translucent; and
(B) said first image and said second image are generated chronologically one after the other with electromagnetic sensors; and
the containers are made of a material that is not transparent or translucent, and/or the bottled liquid is not transparent or translucent.

5. The method according to claim 4, wherein:
said container is oriented with its bottom facing substantially downward during the generation of the images;
between the generation of said first and second images, the container is shaken, preferably by being pivoted one or more times; and
surface matrix sensors for electromagnetic radiation are used as electromagnetic sensors.

6. The method according to claim 5, wherein:
during the image analysis, image elements that are identical in shape and/or position in the images are essentially eliminated as elements that are not essential for the inspection and/or are not taken into consideration;
one of (A) and (B):
(A) the presence of foreign objects is determined only when the analysis of at least two images shows at least one foreign object; and
(B) the presence of foreign objects is determined if the analysis of at least one image shows at least one foreign object;
said first vectoral position is such that the longitudinal axis of said container is at a zero angle with respect to the vertical; and
said second and third vectoral positions are such that the longitudinal axis of said container is at a non-zero angle with respect to the vertical.

7. The method according to claim 6, wherein:
the image area imaged by said opto-electrical sensor is always identical or essentially identical;
for the inspection, the containers are moved past the opto-electrical sensors with a transport system;
the containers are held suspended on the transport system or on grippers on the transport system; and
the containers, to vary their position, are pivoted around an axis parallel to the direction of transport of the transport system.

8. An inspection arrangement for performing the method according to claim 6, said inspection arrangement comprising:
a transport arrangement being configured to orient a container in said first orientation, and being configured to orient the container in said second orientation;
an imaging and processing system comprising:
a first sensor being configured to generate a first image of the container upon the container being in said first orientation;
a second sensor being configured to generate a second image of the container upon the container being in said second orientation; and
a computer system being configured to process and/or compare said first image with said second image to determine if at least one foreign object is present in the liquid.

9. The method according to claim 1, wherein:
said first vectoral position is such that the longitudinal axis of said container is at a zero angle with respect to the vertical; and
said second and third vectoral positions are such that the longitudinal axis of said container is at a non-zero angle with respect to the vertical.

10. An inspection arrangement for performing the method according to claim 9, said inspection arrangement comprising:
a transport arrangement being configured to orient a container in said first orientation, and being configured to orient the container in said second orientation;
an imaging and processing system comprising:
a first sensor being configured to generate a first image of the container upon the container being in said first orientation;
a second sensor being configured to generate a second image of the container upon the container being in said second orientation; and
a computer system being configured to process and/or compare said first image with said second image to determine if at least one foreign object is present in the liquid.

11. An inspection arrangement for performing the method according to claim 1, said inspection arrangement comprising:
a transport arrangement being configured to orient a container in said first orientation, and being configured to orient the container in said second orientation;
an imaging and processing system comprising:
a first sensor being configured to generate a first image of the container upon the container being in said first orientation;
a second sensor being configured to generate a second image of the container upon the container being in said second orientation; and
a computer system being configured to process and/or compare said first image with said second image to determine if at least one foreign object is present in the liquid.

12. The inspection arrangement according to claim 11, wherein each of said sensors is disposed such that said sensors are oriented transverse to the container axis upon generation of an image.

13. A method of inspecting liquid-filled containers, such as bottles and similar containers, said method comprising:
generating a first image of a container with a first sensor upon said container being in a first orientation in which the longitudinal axis of said container is disposed at a first vectoral position with respect to the vertical;
moving said container to a second orientation in which the longitudinal axis of said container is disposed at a second, different, vectoral position with respect to the vertical;
generating a second image of said container with a second sensor upon said container being in said second orientation; and
processing and/or comparing said first image with said second image using a computer system to determine if at least one foreign object is present in the liquid, and during the image analysis, defects in the container are essentially eliminated as elements that are not essential for the inspection and/or are not taken into consideration.

14. The method according to claim 13, wherein:
one of (A) and (B):
(A) the presence of foreign objects is determined only when the analysis of at least two images shows at least one foreign object; and
(B) the presence of foreign objects is determined if the analysis of at least one image shows at least one foreign object;
said first vectoral position is such that the longitudinal axis of said container is at a zero angle with respect to the vertical; and
said second vectoral position is such that the longitudinal axis of said container is at a non-zero angle with respect to the vertical.

15. An inspection arrangement for performing the method according to claim 13, said inspection arrangement comprising:
a transport arrangement being configured to orient a container in said first orientation, and being configured to orient the container in said second orientation;
an imaging and processing system comprising:
a first sensor being configured to generate a first image of the container upon the container being in said first orientation;
a second sensor being configured to generate a second image of the container upon the container being in said second orientation; and
a computer system being configured to process and/or compare said first image with said second image to determine if at least one foreign object is present in the liquid, and, during the image analysis, defects in the container are essentially eliminated as elements that are not essential for the inspection and/or are not taken into consideration.

16. The inspection arrangement according to claim 15, wherein said sensors are disposed along an inspection line on which containers are moved for the generation of said first and second images.

17. The inspection arrangement according to claim 16, wherein said imaging and processing system comprises a third sensor being configured to generate a third image of a container upon the container being in a third orientation in which the longitudinal axis of the container is at a third vectoral position with respect to the vertical different from the second vectoral position.

18. The inspection arrangement according to claim 17, wherein:
said transport arrangement comprises grippers configured to hold containers in a suspended position;
said transport arrangement is configured to pivot containers around an axis parallel or substantially parallel to the direction of transport to vary the orientation of the containers with respect to the vertical; and
said sensors comprise optical scanners and/or cameras or camera systems.

19. The inspection arrangement according to claim 18, wherein said inspection arrangement further comprises:
a container inlet and outlet arrangement being configured to move containers to and from said transport arrangement;
a conveyor being configured to move containers to and from said container inlet and outlet arrangement;
said container inlet and outlet arrangement is configured to be removable from said inspection arrangement to permit movement of containers on said conveyor to bypass said transport arrangement and said inspection apparatus; and
said container inlet comprises a starwheel and a container infeed device configured to space containers to be received by said starwheel, and said container outlet comprises a starwheel, all of which are configured to be removable.

20. The inspection arrangement according to claim 15, wherein:
one of (A) and (B):
(A) the presence of foreign objects is determined only when the analysis of at least two images shows at least one foreign object; and
(B) the presence of foreign objects is determined if the analysis of at least one image shows at least one foreign object;
said first vectoral position is such that the longitudinal axis of said container is at a zero angle with respect to the vertical; and
said second vectoral position is such that the longitudinal axis of said container is at a non-zero angle with respect to the vertical.

21. An inspection arrangement for inspecting liquid-filled containers, such as bottles and similar containers, said inspection arrangement comprising:
at least one inspection station being configured to inspect containers;
a container handling arrangement configured to pick up and move containers along a treatment or inspection line in a linear movement past said at least one inspection station; and
said container handling arrangement comprises:
a movable flexible element;
a plurality of slides connected to said flexible element;
a plurality of grippers, each being slidably, adjustably connected to a corresponding one of said slides; and
each of said grippers being configured to pick up a container at a container infeed area by gripping a container adjacent the container opening and holding the container in a suspended manner.

22. The inspection apparatus according to claim 21, wherein the flexible element is a toothed belt.

23. The inspection apparatus according to claim 22, wherein one of (A), (B), (C), or (D):

(A) the flexible element is held on a guide;
(B) the flexible element is held on a guide; and
the guide, at least in sections, is curved and/or circular and/or arc-shaped and/or straight;
(C) the flexible element is held on a guide;
the guide, at least in sections, is curved and/or circular and/or arc-shaped and/or straight; and
at least one pulley is provided for the flexible element; and
(D) the flexible element is held on a guide;
the guide, at least in sections, is curved and/or circular and/or arc-shaped and/or straight;
at least one pulley is provided for the flexible element; and
said at least one pulley is a toothed belt sprocket wheel.

* * * * *